United States Patent
Veruva et al.

(10) Patent No.: US 12,070,522 B2
(45) Date of Patent: Aug. 27, 2024

(54) MELT BLOWN DRESSING WITH GRADIENT DENSITY

(71) Applicant: Ethicon, Inc., Somerville, NJ (US)

(72) Inventors: Sai Veruva, Somerville, NJ (US);
Jianguo Zhou, Somerville, NJ (US);
Joseph Vliet, Somerville, NJ (US);
Gerard Llanos, Somerville, NJ (US);
Kenneth Keilman, Somerville, NJ (US)

(73) Assignee: Ethicon, Inc., Raritan, NJ (US)

( * ) Notice: Subject to any disclaimer, the term of this patent is extended or adjusted under 35 U.S.C. 154(b) by 1228 days.

(21) Appl. No.: 16/793,104

(22) Filed: Feb. 18, 2020

(65) Prior Publication Data
US 2021/0252185 A1    Aug. 19, 2021

(51) Int. Cl.
| | |
|---|---|
| A61F 13/00 | (2024.01) |
| A61L 15/22 | (2006.01) |
| A61L 15/60 | (2006.01) |
| A61F 13/15 | (2006.01) |

(52) U.S. Cl.
CPC ........ A61L 15/60 (2013.01); A61F 13/00063 (2013.01); A61L 15/225 (2013.01); *A61F 2013/00604* (2013.01); *A61F 2013/00676* (2013.01); *A61F 2013/00863* (2013.01); *A61F 2013/15357* (2013.01); *A61F 2013/15967* (2013.01)

(58) Field of Classification Search
None
See application file for complete search history.

(56) References Cited

U.S. PATENT DOCUMENTS

| | | | |
|---|---|---|---|
| 6,152,943 | A  | 11/2000 | Sawhney |
| 6,165,201 | A  | 12/2000 | Sawhney |
| 6,179,862 | B1 | 1/2001  | Sawhney |
| 6,514,534 | B1 | 2/2003  | Sawhney |
| 6,566,406 | B1 | 5/2003  | Pathak  |
| 6,605,294 | B2 | 8/2003  | Sawhney |
| 6,673,093 | B1 | 1/2004  | Sawhney |
| 6,703,047 | B2 | 3/2004  | Sawhney |
| 6,818,018 | B1 | 11/2004 | Sawhney |
| 7,009,034 | B2 | 3/2006  | Pathak  |
| 7,347,850 | B2 | 3/2008  | Sawhney |
| 8,287,909 | B2 | 10/2012 | Martin  |

(Continued)

FOREIGN PATENT DOCUMENTS

| | | |
|---|---|---|
| EP | 2331854 B1 | 6/2013 |
| EP | 2529044 B1 | 4/2014 |

(Continued)

OTHER PUBLICATIONS

International Search Report dated May 3, 2021 for International Application No. PCT/IB2021/050863.

*Primary Examiner* — Kim M Lewis
(74) *Attorney, Agent, or Firm* — David R. Crichton; Leo B. Kriksunov

(57) ABSTRACT

An absorbable hemostatic nonwoven patch utilizes a biocompatible substrate comprised of melt-blown microfibers as webbed sheets that are layered and bonded/entangled in descending density and ascending porosity; the substrate having a high flexibility, strength and porosity that is suitable for coating cross-linkable active molecules and ability for laparoscopic use or trocar deployment, ultimately for functional use as a highly effective hemostat in addressing problematic bleeding during both open and minimally invasive surgical procedures.

20 Claims, 2 Drawing Sheets

(56) References Cited

U.S. PATENT DOCUMENTS

| | | |
|---|---|---|
| 8,961,544 B2 | 2/2015 | Komlos |
| 9,358,318 B2 | 6/2016 | Gorman |
| 2006/0258995 A1 | 11/2006 | Pendharkar |
| 2009/0104276 A1 | 4/2009 | Andjelic |
| 2009/0264040 A1 | 10/2009 | Emneta |
| 2011/0045047 A1 | 2/2011 | Bennett |
| 2011/0070288 A1 | 3/2011 | Andjelic |
| 2013/0096063 A1 | 4/2013 | Hedrich |
| 2013/0149343 A1 | 6/2013 | Pesnell |
| 2014/0073705 A1 | 3/2014 | Kelly |
| 2014/0178446 A1 | 6/2014 | Zhu |
| 2015/0223928 A1 | 8/2015 | Limem |
| 2015/0351776 A1 | 12/2015 | Swayze |
| 2017/0233913 A1 | 8/2017 | Shimada |

FOREIGN PATENT DOCUMENTS

| | | |
|---|---|---|
| EP | 3255188 B1 | 8/2019 |
| KR | 20160037326 A | 4/2016 |
| WO | 02072163 A1 | 9/2002 |
| WO | WO2007117385 A9 | 2/2008 |
| WO | 2010025219 A1 | 3/2010 |
| WO | 2011037760 A2 | 3/2011 |
| WO | WO2013113906 A1 | 8/2013 |
| WO | WO2017074671 A1 | 5/2017 |

MELT BLOWN DRESSING WITH GRADIENT DENSITY

BACKGROUND

Absorbable hemostatic patches containing two cross-linkable components have been described in the literature, including in US Publication No. 2011/0045047 A1. The cross-linkable components for such patches can be a pair of coreactive compounds or a substrate coated with a coreactive compound having available units that can form covalent crosslinks with the corresponding coreactive group on the substrate and/or the target bleeding site tissue. Plasma derived biologic components that initiate, enhance and/or support the hemostatic cascade to generation of fibrin clots have also been applied onto substrates of various construction and materials.

SUMMARY OF THE INVENTION

The present invention relates to an absorbable hemostatic patch for sealing, and more particularly, to an economically-viable elastic-layered matrix substrate, comprised of melt-blown nonwoven microfibers as webbed sheets that are layered and bonded/entangled in descending density and ascending porosity. The gradient-based construct improves coating characteristics of cross-linkable active molecules, such as reactive polyethylene glycol-based compounds (PEGs) or biologic components, whereas the layering introduces uniquely distributed stiffness in the matrix structure that allows for trocar deployment—all without compromising the overall malleability/conformability and/or the hemostatic effectiveness of the patch. The end-result is a highly functional hemostatic patch that can be utilized in both open and minimally invasive surgical procedures to arrest problematic bleeding.

The present invention is directed to wound dressings comprising a melt-blown multi-layered substrate having at least two major facing surfaces and a coated layer that is applied to at least one of the major facing surfaces of a sealing agent that is selected from the group consisting of co-reactive hydrogel-forming materials, one or more plasma-based hemostatic agents and combinations thereof, wherein the melt-blown substrate has a porosity gradient profile. The substrate is preferably a multi-layered, integrated composite of layers of polymeric materials, each layer having descending density and ascending porosity relative to an adjacent layer. The substrate preferably consists essentially 4 to 14 discrete and integrated layers. Each discrete and integrated layer can be about 0.05-0.2 mm thick. The substrate preferably has, on an overall basis, pores with pore sizes in the range of 0.01-0.5 mm, more preferably the majority of the pores have a pore size diameter in the range of 0.1-0.3 mm.

The total/overall open porosity of the substrate can be in a range from of 30-90%. In one embodiment, the bottom-third of the substrate has an open porosity of about 30%, the middle-third has an open porosity of about 80% and the top-third of the substrate to the coated major surface has an open porosity of about 85%.

The coating preferably is applied so that at least a portion of the coating rests on at least one major surface of the substrate and penetrates to a depth greater than 90% of the thickness substrate, while the overall substrate porosity is greater than 60%. In one embodiment, the coating can penetrate to a depth greater than 95% penetration. In another embodiment, the coating penetrates to a depth of at least 97%. The overall substrate porosity can be greater than 65%, preferably greater than 70%.

In one embodiment, the substrate has a mean stiffness of at least 0.50 N/mm, such as a mean stiffness of about 0.53 N/mm.

In one embodiment, the polymeric materials are selected from biodegradable polymers selected from the group consisting of polyglycolic acid (PGA), poly (lactic-co-glycolic acid) (PLGA), poly(lactic acid) (PLA), (polydioxanone) (PDS), polycarolactone, caprolactone/glycolide copolymers and combinations thereof.

In one embodiment, the polymeric material is a copolymer of glycolide and epsilon-caprolactone (Monocryl), polyglactin 910 (Vicryl) or combinations thereof.

The hydrogel-forming materials can be at least two different multifunctional polymers or polymeric precursors that comprise two or more electrophilic or nucleophilic functional groups. In one embodiment, at least one of the hydrogel-forming materials has two or more nucleophilic functional groups that reacts with an electrophilic functional group on a second hydrogel-forming material to form a covalent bond.

The hemostatic agents can be selected from prothrombin, thrombin, fibrin, fibronectin, Factor (Factor) X/Xa, Factor VII/VIIa, Factor IX/IXa, factor XI/XIa, Factor XII/XIIa, tissue factor, von Willebrand factor, elastin, albumin, platelet surface glycoproteins, vasopressin and vasopressin group consisting of analogs, epinephrine, selectin, plasminogen activator inhibitor, platelet activating agents, synthetic peptides, and any combinations thereof having hemostatic activity.

The present invention is also directed to methods for preparing a wound dressing as described herein by melt blowing microfibers as webbed sheets, layering the melt-blown sheets, and bonding the layers of melt-blown sheets.

The present invention is also directed to methods for sealing a tissue surface by applying the wound dressings as described above on an injured and/or moist tissue surface.

The present invention is directed to an absorbable hemostatic nonwoven patch and wound dressing that utilizes a biocompatible substrate comprised of melt-blown microfibers as webbed sheets that are layered and bonded/entangled in descending density and ascending porosity; with the substrate having a high flexibility, strength and porosity that is suitable for coating cross-linkable active molecules and ability for laparoscopic use or trocar deployment, ultimately for functional use as a highly effective hemostat in addressing problematic bleeding during both open and minimally invasive surgical procedures.

DETAILED DESCRIPTION

Figure 1:
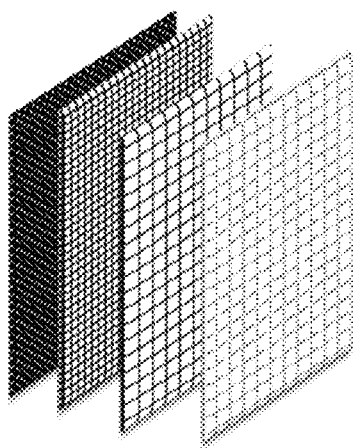
FIG. 1 is an exploded view schematic drawing of the gradient patch in which melt-blown nonwoven sheets are layered in descending density and ascending porosity.
Figure 2:
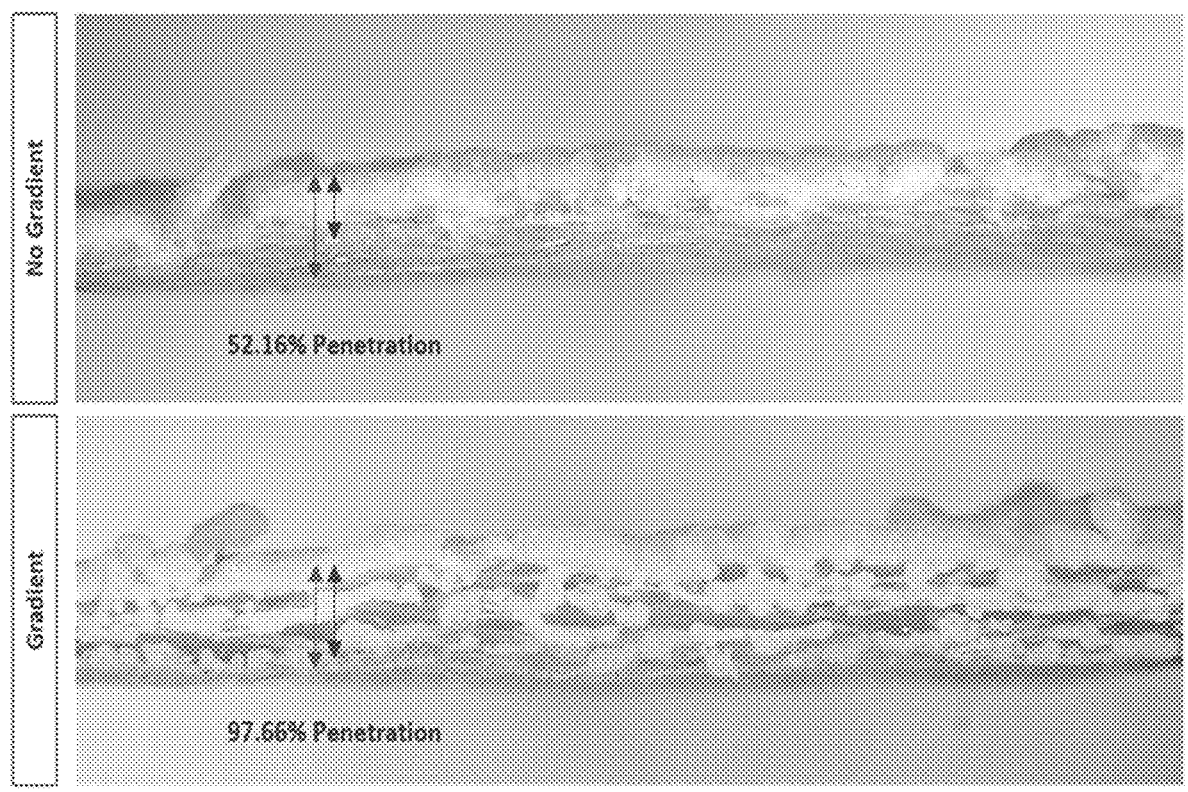
FIG. 2 is microscopy (30×) images of the cross-section of a gradient profiled construct that allowed greater interpenetrated coating in the matrix structure in comparison to clumped/aggregated coating on the non-gradient substrate.

The present invention provides a wound dressing that advantageously forms a matrix that is particularly suited for coating, having a highly porous layer at the surface that increases surface area available for coating as well as allowing deeper coating penetration. Preferably, the wound dressing ultimately provides a means to coat individual melt-blown fibers within the body of a complex nonwoven network instead of aggregating or forming a film layer on the surface.

The preferred wound dressing has a substrate layer characterized by having a tortuous path and high matrix loft throughout the substrate prior to coating. Layering and stacking melt-blown sheets in descending density and ascending porosity results in a complex nonwoven network that not only adds to the mechanical integrity of the matrix but provides the added benefit of allowing blood to percolate while the hydrogel reactive components and/or biologic components hydrate and react to create a seal integrated with the substrate and an external surface. The desired tortuosity throughout the substrate may also prevent the patch from bulging when attempting to arrest higher-pressure bleeding.

The preferred wound dressing exhibits tactility and ease of handling. Due to increased stiffness resulting from the unique layering of the melt-blown sheets, the inventive patch has a sturdy, robust and resilient structure that can provide a haptic advantage during use and compliant on tissue when applied.

The preferred wound dressing is laparoscopically deployable in that the matrix architecture and unique distribution of stiffness in the structure (especially after coating) provides "shape-memory" that allows for the patch to be rolled up, deployed through a trocar, and upon delivery, a return to the original shape without permanent deformation.

The preferred wound dressing is a relatively strong patch that provides good adhesion to tissue. Based on data available, it appears that a higher penetration into the substrate layer of the reactive components and the porous nature at the surface level provides ability for effective adhesion at the patch-tissue interface.

The preferred wound dressing properties can be tailored by managing the number of layers along with fiber structure to allow for specific characteristics, e.g. increasing stiffness with increasing layers, increasing melt blown extrusion process factors, such as drum speed, and distance between the extrusion die surface and collecting drum to change porosity.

The preferred wound dressing has high tissue conformability as a result of the combination of elastic-layered and open-porous interface allowing for high compliance with the tissue if the tissue expands or moves without compromising cohesive properties strengthened by the denser backing.

The preferred wound dressing can have tailored absorption time/biocompatibility. The melt-blown nonwoven matrix can be fabricated using biocompatible and absorbable materials such as Monocryl® with the ability to tailor properties by modulating fiber diameter and polymer structure during melt extrusion and post crystallization treatment respectively (e.g. smaller fiber diameter will absorb faster).

In one embodiment, a nonwoven base substrate is generated from an absorbable and biocompatible polyester material, such as Monocryl®, by extrusion through a linear die containing several hundred small orifices. Convergent streams of hot air attenuate the molten polymer to form extremely fine-diameter fibers. High-velocity air blows the fibers onto a collecting drum, forming one sheet of the melt-blown non-woven fabric. Process factors, such as drum speed and distance between the extrusion die surface and collecting drum, are selected to obtain preferred fiber diameter and orientation, which in-turn governs the resulting pore-size and density of the nonwoven matrix.

The drum width, while dependent on the length of the polymer-extrusion die, is arbitrary and can be scaled up for large-scale manufacture of melt-blown sheets. The drum speed is inversely proportional to the patch density per unit-area, and is inherently associated with fiber diameter, specific surface area and the overall porosity in the layer. The collector distance also affects matrix characteristics as increasing the gap between the polymer-extrusion die and the collecting drum better randomizes fiber thickness and orientation on the web.

The present invention identified preferred drum speeds in the range of 4-20 RPM and distances in the range of 10 to 40 inches. Varying combinations within these ranges were utilized to generate layers with descending density and ascending porosity. Collector drum distance is set in the range of 10-40 inches, with preferred settings for each layer as identified to achieve a target porosity distribution in the matrix architecture.

The ranges were established using Monocryl® for which the material properties (e.g. 1.67 intrinsic viscosity) may affect fiber characteristics to a small degree, that in-turn play into porosity, density and stiffness of the overall matrix. However, the ranges should showcase the same trends irrespective of material specifics (for example, increasing the drum speed will reduce patch density for both Monocryl® and Vicryl®, and at the very least, the ranges we determined are viable starting points). Other biodegradable polymers of interest that can be melt-blown include and are not limited to PGA, PLGA, PLA, PDS, PCL and caprolactone/glycolide copolymers.

These ranges are one set of methods to generate all desired density and porosity in the matrices that were found to be functional hemostats. However, one can achieve these density and porosity characteristics by modulating other process factors during melt blown extrusion (e.g. screw speeds and extrusion temperatures).

The present invention, identified preferred thickness in the range of 0.30-2.5 mm, more preferably 0.6-1.1 mm, most preferably 0.9-1.1 mm. More important than thickness which has a wide range, the gradient and top-porous structure is generated through layering individual sheets, which are all less than 0.5 mm in thickness, most preferably in the 0.05-0.2 mm range.

The present invention identified a preferred pore size distribution, based on micro-CT analysis, in the range of 0.01-0.5 mm, with majority of the pores in the range of 0.1-0.3 mm. Additionally from the micro-CT analysis, the invention identified the total open porosity of the matrix to range from of 30-90%. The wide range in total porosity is attributed to the gradient-based layering of the construct in which the porosity of the bottom-third of the matrix is approximately 30%, the middle-third is 80% and the top-third (surface) is 85%.

Melt blowing these polymers provides a unique advantage in generating ultra-fine fibers; in contrast, spun-bonded filaments do not have the fineness of the melt-blown method. The present invention of the melt-blown nonwoven identified fine fibers and a diameter in the in the range of 1-250 micrometers in all of the layers, preferably in the range of 1-90 microns. Given the gradient-based architecture, the finer fibers are generally preferred to be in upper regions of the matrix, near the surface. To that regard, the most preferred fiber diameter range of the bottom-third of the matrix was determined to be 10-80 micrometers, the middle-third to be 10-40 micrometers and the top-third (surface) to be 1-30 micrometers.

Each sheet of the melt-blown polyester-based nonwoven, once produced having the for desired density and porosity, is used as a building-block in the multi-layered, gradient-based patch concept.

One advantage of the gradient design described herein is production of a complex tortuous path for any substance flowing through the matrix; it is envisioned that blood will percolate from a coated layer that is placed in contact with a moist tissue surface and clot before reaching the densest, and preferably water-impermeable, layer that is furthest away from the coated layer. Additionally, this matrix has a high loft that is relatively soft/fluffy and "cushion-like" that an end user may find useful and easy-to-handle.

The gradient concept is essentially a multi-layered composite of layers built with descending densities and ascending porosities (FIG. 1). Each layer of melt-blown polyester-based nonwoven sheet is generated on the collecting drum and allowed to partially crystallize for 15 minutes under an industrial blower. Next, a subsequent over-layer with either less density and/or more porosity is applied over a prior layer and allowed to bond with the partially crystallized prior layer.

In an alternative embodiment, individual melt-blown layers can also be generated separately and then stacked and bonded using either thermal or ultrasonic methods.

In one embodiment, the matrix has at least four discrete layers and not more than discrete fourteen layers wherein each layer was about 0.05-0.2 mm thick. A minimal number of layers (with or without gradient) is necessary so the matrix has structural integrity whereas there is also a limit to how many melt-blown sheets can be layered before the matrix substrate becomes too large and too stiff for practical application.

A substrate having four layers with no gradient profile results in a drastically different topography compared to seven or fourteen layers. Applicants discovered that by increasing the number of layers increases depth of voids/spaces that coatings may be able to penetrate into. Relative analysis of the 3-D models (Table 1) revealed 7-layers and 14-layers increased the maximum height of the pore or void space at the surface by about 45% and 200%, respectively. The relative surface area and volume also increased substantially in the multi-layered gradient constructs.

TABLE 1

|  | Maximum Height (micrometers) | Surface Area (micrometers$^2$) | Volume (micrometers$^3$) |
| --- | --- | --- | --- |
| 4-layer non-gradient | 1477 | 38,041,772 | 978,473,280 |
| 7-layer gradient | 2146 | 60,072,320 | 3,541,309,440 |
| 14-layer gradient | 4417 | 60,933,412 | 7,634,171,904 |
| None VS 7-layer (% Δ) | 45.29 | 57.9 | 261.9 |
| None VS 14-layer (% Δ) | 199.1 | 60.2 | 680.2 |
| 7-layer VS 14-layer (% Δ) | 105.8 | 1.43 | 115.6 |

Coating a matrix substrate without a gradient profile resulted in poor penetration and aggregation or clumping of material, whereas the matrix with a gradient profile displayed effective coating of individual fibers and improved penetration into the matrix. Advanced microscopy and depth composition analysis showed the ascending porosity resulted in unique in-depth coating, encapsulating more nonwoven fibers, individually, instead of aggregating at the top of the surface. Microscopy of the cross-section at 30× magnification confirmed the gradient construct allowed for interpenetrated coating in the matrix structure in comparison to clumped/aggregated coating on the matrix with no gradient; the coating penetrated 42% more into the matrix with a gradient construct. The images also suggested mass-dependent coating on the gradient-based surface can better preserve the matrix height and loft, whereas the same coating may compress the matrix without a gradient.

To further corroborate matrix characteristics, porosity was assessed via micro-CT imaging and analysis (Table 2).

TABLE 2

| Porosity assessment via micro-CT imaging and analysis. | | | |
| --- | --- | --- | --- |
| ID | Patch Condition | Porosity (%) | % Change |
| 1 | No gradient | 85 | — |
| 2 | No gradient - coated | 62 | — |
| 3 | Gradient | 90 | 5 (compared to 1) |
| 4 | Gradient - coated | 72 | 10 (compared to 2) |

Gradient substrates resulted in 5% greater porosity throughout the matrix, despite higher bulk material. Gradient patches, after coating, resulted in 10% greater porosity throughout the matrix, despite higher bulk material.

In one embodiment, a hemostatic patch comprised of a nonwoven, gradient-based melt-blown substrate is combined with a cross-linkable coating. Exemplary melt-blown microfiber sheets are made using an absorbable and biocompatible polyester material, such as Monocryl® (I.V. of 1.67), and layer onto a collecting drum. Each layer, after melt extrusion, is allowed to partially crystallize for a preferred 15 minutes under an air-circulating fan. In the most-preferred embodiment, the sequential layer is overlaid immediately after a fifteen 15 minute cool-down, at which point the prior partially crystallized former layer bonds at both fiber point-to-point contacting regions as well as creating fiber entanglements. In this embodiment, the entangled, layered structure is once again allowed to partially crystallize, and the cycle is repeated to build the most-preferred gradient-based matrix as described in Table 5.

TABLE 5

| Sequential layering of melt-blown nonwoven sheets | | | | |
| --- | --- | --- | --- | --- |
| | Gradient Layer Generation | Collector speed (rpm) | Collector distance (in) | Layers (revs) |
| 1 | Layer 1 | 4.2 | 25 | 1 |
| 2 | Layer 2 | 8.3 | 12 | 1 |
| 3 | Layer 3 | 8.3 | 25 | 1 |
| 4 | Layer 4 | 11 | 25 | 1 |
| 5 | Layer 5 | 13.7 | 25 | 1 |
| 6 | Layer 6 | 16.6 | 25 | 1 |
| 7 | Layer 7 | 18.6 | 30 | 1 |

The final construct is allowed to fully crystallize in a vacuum chamber for at least 12 hours, followed for storage in moisture-free environments.

The most-preferred matrix has 7-layers and a coating penetration depth greater than 90% of thickness, more preferably greater than 95% penetration, most preferably at least 97% and a total matrix porosity greater than 60%, more preferably greater than 65%, most preferably about 72%, respectively. The most-preferred patch had a mean stiffness of 0.53 N/mm.

In an alternative embodiment, each melt-blown sheet/layer can be generated separately and allowed to crystallize for at least 12 hours in a vacuum chamber. Then, the layers are stacked and bonded either thermally or ultrasonically at pin-hole-sized contact points across the matrices. The dressing of the present invention includes a carrier layer having a plurality of fibrous sublayers that contain coreactive, crosslinkable components. Cross-linkable actives, such as reactive PEGS, are preferably coated in sequence with or without buffers and additives to develop the fully functional hemostat. A top sublayer is provided with a coreactive and crosslinkable component and/or at least one plasma derived or plasma related hemostatic agent, fibrinogen is preferred. In another embodiment, the hemostatic agent may be thrombin or fibrinogen, each individually or in combination.

Exemplary plasma derived (or related) hemostatic agents include proteins and peptides, and thus do not limit to only natural, as the agents may be recombinant, or synthetic forms of; prothrombin, thrombin, fibrin, fibronectin, Factor (Factor) X/Xa, Factor VII/VIIa, Factor IX/IXa, factor XI/XIa, Factor XII/XIIa, tissue factor, von Willebrand factor, elastin, albumin, platelet surface glycoproteins, vasopressin and vasopressin group consisting of analogs, epinephrine, selectin, plasminogen activator inhibitor, platelet activating agents, synthetic peptides, and any combinations thereof having hemostatic activity.

The carrier sublayers can be in the form of non-woven materials. Exemplary materials of construction are synthetic polymers. The substrate may be comprised of components selected from aliphatic polyester polymers and/or copolymers of one or more monomers selected from the group consisting of D-lactic acid, L-lactic acid, lactide (including L-, D-, meso forms), glycolic acid, glycolide, caprolactone, p-dioxanone and trimethylene carbonate and mixtures or blends thereof.

The substrate may alternatively, or additionally, be comprised of layers of fabric of aliphatic polyester polymers, copolymers, or blends thereof. The aliphatic polyesters are typically synthesized in a ring opening polymerization of monomers including, but not limited to, lactide (including L-, and D-, meso forms), glycolic acid, glycolide, caprolactone, p-dioxanone (1,4-dioxan-2-one), and trimethylene carbonate (1,3-dioxan-2-one). The aliphatic polyesters, in some cases, can be made by polycondensation of for instance, D-lactic acid, L-lactic acid and/or glycolic acid. In one form, the fabric comprises a copolymer of glycolide and lactide, in an amount ranging from about 70 to 95% by molar basis of glycolide and the remainder lactide.

The porous substrate of the dressing has openings or pores over at least a portion of a surface thereof. As described in more detail below, suitable materials for forming the porous substrate include, but are not limited to fibrous structures. In embodiments, the pores may be in sufficient number and size so as to interconnect across the entire thickness of the porous substrate.

One or more sublayers of the porous substrate can be at least 0.1 cm thick, in certain embodiments from about 0.2 to about 1.5 cm thick. The size of the pores in the sublayers of the porous substrate can be from about 2 micrometers to about 300 micrometers, in embodiments from about 50 micrometers to about 150 micrometers. It is envisioned that the pores of the sublayers of the substrate may be arranged in any manner in the substrate. For example, the pores may be configured in a random or uniform manner. In some embodiments, the pores may be formed with the use of calcium or copper alginate to create a honey-comb shaped porous substrate. In still other embodiments, the pores may be configured to create a gradient in the porous substrate. The gradient may further enhance the porous substrates ability to absorb the physiologic fluid and direct the migration of the physiological fluid carrying the first coreactive component towards the second coreactive component.

In one embodiment, the substrate has a first coreactive component applied onto a first sublayer and a second coreactive component applied thereto. The terms "first coreactive component" and "second coreactive component" each means a polymer, functional polymer, macromolecule, small molecule, or crosslinker that can take part in a reaction to form a network of crosslinked molecules, such as, a hydrogel.

In one embodiment, each of the first and second coreactive components is multifunctional, meaning that it comprises two or more electrophilic or nucleophilic functional groups, such that, for example, a nucleophilic functional group on the first coreactive component may react with an electrophilic functional group on the second coreactive component to form a covalent bond. At least one of the first or second coreactive components includes more than two functional groups, so that, as a result of electrophilic-nucleophilic reactions, the precursors combine to form crosslinked polymeric products. Such reactions are referred to as "crosslinking reactions".

In certain embodiments, each of the first and second coreactive components includes only one category of functional groups, either only nucleophilic groups or only electrophilic functional groups, so long as both nucleophilic and electrophilic precursors are used in the crosslinking reaction. Thus, for example, if the first coreactive component has nucleophilic functional groups such as amines, the second coreactive component may have electrophilic functional groups such as N-hydroxysuccinimides. On the other hand, if first coreactive component has electrophilic functional groups such as sulfosuccinimides, then the second coreactive component may have nucleophilic functional groups such as amines or thiols. Thus, functional polymers such as proteins, poly(allyl amine), styrene sulfonic acid, or amine-terminated di- or multifunctional poly(ethylene glycol) ("PEG") can be used.

The first and second coreactive components may have biologically inert and water soluble cores. When the core is a polymeric region that is water soluble, preferred polymers that may be used include: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly (saccharides), such as dextran, chitosan, alginates, carboxymethylcellulose, oxidized cellulose, hydroxyethylcellulose, hydroxynethylcellulose, hyaluronic acid; and proteins such as albumin, collagen, casein, and gelatin. The polyethers and more particularly poly(oxyalkylenes) or poly(ethylene glycol) or polyethylene glycol are especially useful. When the core is small molecular in nature, any of a variety of hydrophilic functionalities can be used to make the first and second coreactive components water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

In certain embodiments, both the first and second coreactive components may be large molecules that are capable of cross-linking. For example, in embodiments, one of the precursors may be a multi-functional PEG having a molecular weight of from about 2,000 to about 20,000 Daltons. This multi-functional PEG, in embodiments possessing electrophilic groups, may be reacted with a collagen having a molecular weight of about 100,000 Daltons. In other embodiments, a gelatin having a molecular weight of from about 50,000 to about 100,000 Daltons may be used in place of the collagen.

In an alternative embodiment, the coreactive components and buffering agent are provided on a patch. An exemplary scaling patch/pad comprises: PEG-NH2*HCl and PEG-NHS, a buffering salt agent, preferably as an alkaline buffer (Borax) deposited on an absorbable substrate.

If it is desired that the biocompatible crosslinked polymer resulting from the reaction of the first and second coreactive components be biodegradable or absorbable, one or more of the first and second coreactive components may have biodegradable linkages present between the functional groups. The biodegradable linkage optionally also may serve as the water soluble core of one or more of the precursors. In the alternative, or in addition, the functional groups of the first and second coreactive components may be chosen such that the product of the reaction between them results in a biodegradable linkage. For each approach, biodegradable linkages may be chosen such that the resulting biodegradable biocompatible crosslinked polymer will degrade, dissolve or be absorbed in a desired period of time. Preferably, biodegradable linkages are selected that degrade under physiological conditions into non-toxic products.

The biodegradable linkage may be chelates or chemically or enzymatically hydrolyzable or absorbable. Illustrative chemically hydrolyzable biodegradable linkages include polymers, copolymers and oligomers of glycolide, d-lactide, lactide, caprolactone, dioxanone, and trimethylene carbonate. Illustrative enzymatically hydrolyzable biodegradable linkages include peptidic linkages cleavable by metalloproteinases and collagenases. Additional illustrative biodegradable linkages include polymers and copolymers of poly(hydroxy acid)s, poly(orthocarbonate)s, poly(anhydride)s, poly(lactone)s, poly(amino acid)s, poly(carbonate)s, poly(saccharide)s and poly(phosphonate)s. In embodiments, the biodegradable linkage may contain ester linkages. Some non-limiting examples include esters of succinic acid, glutaric acid, propionic acid, adipic acid, or amino acids, as well as carboxymethyl esters.

In certain embodiments, a multifunctional electrophilic polymer such as a multi-arm PEG functionalized with multiple NHS groups may be used as a first coreactive component, and a multifunctional nucleophilic component such as trilysine may be used as a second coreactive component. In other embodiments, a multifunctional electrophilic polymer such as a multi-arm PEG functionalized with multiple NHS groups may be used as a first coreactive component, and a multifunctional nucleophilic polymer such as collagen and/or a collagen derivative may be used as a second coreactive component. The multi-arm PEG functionalized with multiple NHS groups can for example have four, six or eight arms and have a molecular weight of from about 5,000 to about 25,000. Many other examples of suitable first and second precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire content of each of which is incorporated herein by reference.

For the patch embodiment, the coreactive components can be deposited upon the matrix as individual layers. Alternatively, the coreactive components can be deposited as a mixture. The ordering of layers may change, but the preferred order scaling patch or pad comprising PEG-NH2*HCl (or any other hydrohalide), PEG-NHS, and a buffering salt (such as sodium tetraborate, MES, TRIS, Bis-Tris, sodium bicarbonate), with the matrix, then a layer of buffering salt, a layer of protected PEG-amine and a layer of the PEG-NHS. Furthermore, the number of arms and molecular weight of materials may change, but 4-arm-10K-NH2*HCl and 4-arm-10K-NHS are preferred variants from an efficacy and stability standpoint. The embodiment was evaluated with different order of coating. Performance and stability is greatly impacted by the location of the deposited buffer on the matrix using the spray-coating process. When buffer was deposited below both PEGs (i.e., furthest away from the tissue when matrix is applied), the performance and stability were optimal.

The first coreactive component may be applied to the porous substrate using any suitable method known to those skilled in the art, including, but not limited to spraying, brushing, dipping, pouring, laminating, etc. In embodiments, the first coreactive component may be applied as a coating on the substrate in any concentration, dimension and configuration capable of forming a hemostatic dressing. In embodiments, the first coreactive component coating may penetrate the pores of the porous substrate. In embodiments, the first coreactive component may be applied to the porous substrate as a film that is laminated onto at least one side of the substrate.

The second coreactive component likewise may be applied to the porous substrate using any suitable method known to those skilled in the art, including, but not limited to spraying, brushing, dipping, pouring, laminating, etc. In still other embodiments, the second coreactive component may be applied to the porous substrate in solution followed by evaporation or lyophilization of the solvent. In embodiments, the second coreactive component may be applied to the porous substrate as a coating on at least one side of the substrate or as a film laminated onto at least one side of the substrate.

During use, the patch dressing is oriented with the coreactive components applied directly onto the tissue. In embodiments, the first and second portions may be distinguishable from one another by the addition of contrast dyes, surface texturing, coloring or other visual cues. Upon contact with tissue, such as, for example, injured tissue, the dressing will soak up physiological fluid and the first coreactive component will be dissolved by the fluid. As the fluid wicks into and migrates through the dressing, it will carry the dissolved first coreactive component into the second coreactive component and buffering agent. Eventually, the first and second coreactive components will react to form a biocompatible cross linked material, thereby assisting tissue ingrowth and remodeling as the scaffold degrades. In some embodiments, the biocompatible cross linked material produced by reaction of the first and second coreactive components also provide the dressing with anti-adhesive properties.

The following examples are provided for illustrative purposes only and are not intended to limit the scope of the present disclosure.

EXAMPLES

Improved percolation of blood within the substrate was exemplified in an ex vivo bleeding model in which the gradient condition was highly effective in arresting bleeding. The gradient patch also became highly conformable after hydration and adhered to the tissue well. A qualified peel test confirmed substantially higher tissue adhesion relative to a fibrin clot forming patch.

Patches with sub-par performance were identified in an ex vivo bleeding model. Applicants discovered that the number of layers affected efficacy: 5 or fewer layers resulted in cohesive and adhesive failures, whereas 14 or more layers resulted in high adhesive failures; 7-layers was identified to be most-preferred.

The final uniqueness to this construct is attributed to the matrix stiffness and ability for trocar deployment. The matrix architecture and unique distribution of stiffness in the structure (especially after coating) provides "shape-memory" that allows for the patch to be rolled up and deployed through a trocar without deforming. To test this, a 2×2" patch was rolled up around tip of 11 mm trocar (Endopath® XCEL Bladeless Trocar) and inserted via Instron followed by measuring the force to push through.

Mean stiffness, insertion force and mean force were measured through the trocar: the patches with and without gradient had less mean force during trocar deployment and subsequently less deformation compared to a non-woven, non-gradient substrate. The gradient profiled substrate had high stiffness, low insertion force and low mean force (Table 3).

TABLE 3

| Sample | Patch Characteristics Mean Stiffness (N/mm) | Trocar Deployment Insertion Force (N) | Mean Force (N) |
| --- | --- | --- | --- |
| Non-Woven Non-Gradient | 0.05 | 5.51 | 1.83 |
| Gradient | 0.53 | 3.24 | 1.65 |
| No Gradient | 0.27 | 3.74 | 1.24 |

The gradient patch was also observed post-deployment (roll-opening after insertion) and assessed for deformation based on maximum lift at edges (Table 4).

TABLE 4

| Sample | Trocar Deployment (−/+) | Deformation (mm) | Comments |
| --- | --- | --- | --- |
| Fibrin Sealant Patch | − | N/A | Did not unfold at all |
| No Gradient | ++ | 20 | |
| Gradient | +++ | 9 | |

Trocar Deployment Legend
− Roll did not open
+ Roll opened delayed and/or not-fully
++ Roll opened quickly
+++ Roll opened very quickly Coating Process Example A 2-inch by 4-inch melt-blown gradient-based matrix is either ultrasonically spray-coated (solubilized method) or dip-coated (insoluble method) with a light-layer of buffer that embeds deep into the porous substrate.

Working examples include a 1.25 mg/cm$^2$ of sodium borate, 2 mg/cm$^2$ Bis-Tris or 1 mg/cm$^2$ of sodium bicarbonate.

Then, 15 mg/cm$^2$ of 4-arm-PEG-Amine-HCl (MW:10 Kda) is ultrasonically coated, followed by 18 mg/cm$^2$ of 4 arm-PEG-SG (MW:10 Kda)

The gradient construct allows for unique deposition of the cross-linkable actives, deep into the matrix, that ultimately results in a highly effective hemostat.

We claim:

1. A wound dressing comprising a melt-blown multi-layered substrate having at least two major surfaces and a coated layer that is applied to at least one of the major surfaces of a sealing agent that is selected from the group consisting of co-reactive hydrogel-forming materials, one or more plasma-based hemostatic agents and combinations thereof, wherein the melt-blown substrate has a porosity gradient profile.

2. The wound dressing according to claim 1 wherein the substrate is a multi-layered, integrated composite of layers of polymeric materials, each layer having descending density and ascending porosity relative to an adjacent layer.

3. The wound dressing according to claim 2, wherein the substrate consists essentially 4 to 14 discrete and integrated layers.

4. The wound dressing according to claim 3, wherein each discrete and integrated layer is about 0.05-0.2 mm thick.

5. The wound dressing according to claim 1, wherein substrate has, on an overall basis, a pore size diameter in the range of 0.01-0.5 mm.

6. The wound dressing according to claim 5, wherein a majority of the pores have a pore size diameter in the range of 0.1-0.3 mm.

7. The wound dressing according to claim 1, wherein a total open porosity of the substrate is in a range from of 30-90%.

8. The wound dressing according to claim 7 having a mean stiffness of at least 0.50 N/mm.

9. The wound dressing according to claim 1, wherein the bottom-third of the substrate has an open porosity of about 30%, the middle-third of the substrate has an open porosity of about 80% and the top-third of the substrate to the coated major surface has an open porosity of about 85%.

10. The wound dressing according to claim 1, wherein the coating rests on at least one major surface of the substrate and penetrates to a depth greater than 90% of the thickness substrate and the overall substrate porosity is greater than 60%.

11. The wound dressing according to claim 10, wherein the coating penetrates to a depth greater than 95% penetration.

12. The wound dressing according to claim 10, wherein the coating penetrates to a depth of at least 97%.

13. The wound dressing according to claim 12, wherein the overall substrate porosity is greater than 70%.

14. The wound dressing according to claim 13 having a mean stiffness of about 0.53 N/mm.

15. The wound dressing according to claim 10, wherein the overall substrate porosity is greater than 65%.

16. The wound dressing according to claim 1, wherein the polymeric materials are selected from biodegradable polymers selected from the group consisting of polyglycolic acid (PGA), poly (lactic-co-glycolic acid) (PLGA), poly(lactic acid) (PLA), (polydioxanone) (PDS), polycaprolactone, caprolactone/glycolide polyesters and combinations thereof.

17. The wound dressing according to claim 1, wherein the polymeric material is a copolymer of glycolide and epsilon-caprolactone (Monocryl), polyglactin 910 (Vicryl) or combinations thereof.

18. The wound dressing according to claim 1, wherein the hydrogel-forming materials are each at least two different multifunctional polymers or polymeric precursors that comprise two or more electrophilic or nucleophilic functional groups.

19. The wound dressing according to claim 1, wherein the hemostatic agents are selected from prothrombin, thrombin, fibrin, fibronectin, Factor (Factor) X/Xa, Factor VII/VIIa, Factor IX/IXa, factor XI/XIa, Factor XII/XIIa, tissue factor, von Willebrand factor, elastin, albumin, platelet surface glycoproteins, vasopressin and vasopressin group consisting of analogs, epinephrine, selectin, plasminogen activator inhibitor, platelet activating agents, synthetic peptides, and any combinations thereof having hemostatic activity.

20. The wound dressing according to claim 19, wherein at least one of the hydrogel-forming materials has two or more nucleophilic functional groups that reacts with an electrophilic functional group on a second hydrogel-forming material to form a covalent bond.

* * * * *